United States Patent [19]

Cole-Hamilton et al.

[11] Patent Number: 4,604,473

[45] Date of Patent: Aug. 5, 1986

[54] PREPARATION OF METAL ALKYLS

[75] Inventors: David J. Cole-Hamilton, Ormskirk; Anthony C. Jones, St Helens; John B. Mullin, West Malvern, all of England

[73] Assignee: The Secretary of State for Defence in Her Britannic Majesty's Government of the United Kingdom of Great Britain and Northern Ireland, London, England

[21] Appl. No.: 620,256

[22] Filed: Jun. 13, 1984

[30] Foreign Application Priority Data

Jun. 17, 1983 [GB] United Kingdom ............... 8316605

[51] Int. Cl.$^4$ .............................................. C07F 5/00
[52] U.S. Cl. ...................................................... 556/1
[58] Field of Search ......................... 260/429 R; 556/1

[56] References Cited

U.S. PATENT DOCUMENTS 1,938,179 12/1933 Groll ................. 260/429 R
3,318,931 5/1967 Dötzer et al. ................. 260/429 R

FOREIGN PATENT DOCUMENTS 2123423 2/1984 United Kingdom ............ 260/429 R
2175795 3/1984 United Kingdom .
466238 11/1975 U.S.S.R. ......................... 260/429 R
388563 9/1976 U.S.S.R. ......................... 260/429 R

OTHER PUBLICATIONS

Kharasch et al., Grignard Reactions of Nonmetallic Substances, Prentice-Hall, Inc., N.Y. pp. 45-49 (1954).
Nesmeyanov et al., The Organic Compounds of Boron, Aluminum, Gallium, Indium and Thallium, North-Holland Publ. Co., pp. 506-507 (1967).
Dennis et al., JACS 54 182 (1932).
Chemical Abstracts 27, 2646-264 (1933).

Primary Examiner—Helen M. S. Sneed
Attorney, Agent, or Firm—Cushman, Darby & Cushman

[57] ABSTRACT

A method of producing a trialkyl gallium compound $(R_A)_3Ga$, where $R_A$ is selected from methyl and ethyl, includes the step of reacting a gallium trihalide with a Grignard reagent of formula $R_A$ Mg Q, where Q is a halogen, the reaction being carried out in the presence of an ether of the formula $R_1R_2O$ having a boiling point at least 50 Celsius degrees above that of the trialkyl gallium compound $(R_A)_3Ga$, wherein $R_1$ and $R_2$ are organic radicals at least one of which has at least 5 carbon atoms.

The organic radicals $R_1$ and $R_2$ may be aromatic and/or aliphatic radicals. They are preferably alkyl or phenyl radicals. Preferably $R_1R_2O$ is an ether having a boiling point more than 100° C. above that of the trialkyl gallium compound. The radicals $R_1$ and $R_2$ may each independently have from 1 to 14 carbon atoms but preferably together $R_1$ and $R_2$ have between seven and twelve carbon atoms inclusive.

Desirably, $R_1R_2O$ is di-isopentyl ether (3,3-dimethylpropyl) ether. Other examples of $R_1R_2O$ are diphenyl ether and anisole (methylphenyl ether). Preferably, Q is iodine and the gallium trihalide is a chloride.

10 Claims, No Drawings

PREPARATION OF METAL ALKYLS

FIELD OF THE INVENTION

The present invention relates to the preparation of metal alkyls useful in the preparation of compound semi-conductor materials.

BACKGROUND OF THE INVENTION

Compound semiconductor materials, eg materials such as gallium arsenide, indium phosphide, gallium phosphide and cadmium mercury telluride, are well known materials having uses in the electronics industry in such applications as microwave oscillators, semiconductor light emitting diodes and lasers, and infrared detectors.

Such materials have been made in the past by forming, usually on a substrate crystal, one or more active layers, by the method of vapour phase epitaxy (VPE).

It has been known for some time to produce by VPE compound semiconductors of the form $M^A Q^A$ where $M^A$ is Group III element and $Q^A$ is Group V element by reacting a trialkyl of the element $M^A$ with a gaseous compound, eg a hydride, of the Group V element $Q^A$. This method is a suitable method of preparing gallium arsenide from $Ga(CH_3)_3$ and $AsH_3$ for example.

Consequently, trialkyl gallium compounds, in particular trimethyl gallium, have become important in the production of semiconductor materials.

It is well known to those skilled in the art that the presence of impurities in semiconductor materials has a profound effect on the electrical and other properties of the materials. In order to control the properties it is therefore desirable to produce such materials in a high purity form. This means that the precursor materials such as trialkyl gallium compounds used in the manufacture of the semiconductor materials are desirably as pure as possible.

The reaction between gallium trichloride and a Grignard reagent containing an alkyl radical is known but has not hitherto been used for the preparation of trialkyl gallium compounds. This is because the reaction has been carried out is diethyl ether as solvent and has resulted in the formation of trialkyl gallium-diethyl ether adducts. Such adducts cannot be broken down directly into the trialkyl gallium compound without severe contamination from the ether.

SUMMARY OF THE INVENTION

The present invention provides a method for producing a trialkyl gallium compound $(R_A)_3Ga$ wherein the alkyl groups $(R_A)$ are selected independently from methyl and/or ethyl. The method includes the step of reacting a gallium trihalide with a Grignard reagent having the formula $R_AMgQ$ wherein the formula Q is halogen. The reaction is carried out in the presence of an ether having the formula $R_1R_2O$ wherein the ether formula $R_1$ and $R_2$ are organic radicals such at least one of $R_1$ and $R_2$ has at least five carbon atoms. Further, the ether has a boiling point at least 50° C. above that of the trialkyl gallium compound $(R_A)_3Ga$.

The method further includes a subsequent step wherein, as a vapor, the adduct of the initial step is heated and the trialkyl gallium compound is separated off.

In the present method, the organic radicals $R_1$ and $R_2$ may be aromatic and/or aliphatic radicals. Preferably, $R_1$ and $R_2$ are alkyl or phenyl radicals. The radicals $R_1$ and $R_2$ may each have independently have from 1 to 14 carbon atoms. More advantageously, and more preferably, together $R_1$ and $R_2$ have between 7 and 12 carbon atoms inclusive. Preferably, $R_1R_2O$ is an ether having a boiling point more than 100° C. above that of the trialkyl gallium compound.

DETAILED DESCRIPTION OF THE INVENTION

The present invention provides a method of producing a trialkyl gallium compound having the formula $(R_A)_3Ga$ wherein the formula $R_A$ is selected from methyl and ethyl. The method includes Step A wherein a gallium trihalide is reacted with a Grignard reagent having the formula $R_AMgQ$ wherein the formula Q is a halogen. The reaction is carried out in the presence of an ether having a boiling point at least 50° C. above that of the trialkyl gallium compound $(R_A)_3Ga$, wherein the ether has the formula $R_1R_2O$ and wherein the latter formula $R_1$ and $R_2$ are organic radicals, and at least one of $R_1$ and $R_2$ has at least 5 carbon atoms.

The organic radicals $R_1$ and $R_2$ may be aromatic and/or aliphatic radicals. They are preferably alkyl or phenyl radicals. Preferably $R_1R_2O$ is an ether having a boiling point more than 100° C. above that of the trialkyl gallium compound. The radicals $R_1$ and $R_2$ may each independently have from 1 to 14 carbon atoms but preferably together $R_1$ and $R_2$ have between seven and twelve carbon atoms inclusive.

Desirably, $R_1R_2O$ is di-isopentyl ether (3,3-dimethylpropyl)ether. Other examples of $R_1R_2O$ are diphenyl ether and anisole (methylphenyl ether). Preferably, Q is iodine and the gallium trihalide is a chloride.

The main product of Step A used in the method according to the present invention is an adduct of the trialkyl gallium $(R_A)_3Ga$ and the ether $R_1R_2O$. However, in contrast to the known Grignard reaction mentioned above, the reaction of Step A provides an adduct as a product; the adduct may be converted directly into the radical-free trialkyl gallium in a high purity form in a single step. Furthermore, this conversion may be carried out directly using the product of the Grignard reaction in its production vessel without further separation from the contents of the vessel such as, for example, the reagents used in its formation.

The adduct may be converted into the radical-free trialkyl gallium compound by Step B as follows:

heating the adduct $(R_A)_3Ga.OR_1R_2$ as a vapour, and separating the trialkyl gallium compound by fractional distillation of its vapour.

Preferably, Step B is preceded by the removal of volatile impurities by evacuation or distillation at a temperature below the decomposition temperature of the adduct $(R_A)_3Ga.R_1R_2O$.

In Step A specified above the Grignard reaction may be carried out at room temperature (20° C.), or preferably at an elevated temperature eg 70°-110° C. In the latter case the elevated temperature used serves to remove volatile impurities prior to dissociation of the adduct in Step B.

An Example of a method embodying the present invention will now be described in detail.

EXAMPLE

Trimethyl gallium in pure form was produced by the following method.

Di-isopentyl ether was first dried over sodium wire and then redistilled.

Methyl magnesium iodide was then prepared in the ether as follows.

Methyl iodide (27 ml, 0.43 mol) was added to a suspension of magnesium turnings (10.2 g, 0.42 mol) in the di-isopentyl ether (200 ml). The rate of addition of methyl iodide was such that the mixture remained very hot throughout the addition and did not require external heating.

The following reaction was then carried out in an atmosphere of dry nitrogen.

The solution of methyl magnesium iodide in di-isopentyl ether was added over a period of one hour to a stirred solution of anhydrous gallium trichloride (25 g, 0.14 mol) in di-isopentyl ether (50 ml). The rate of addition of the Grignard solution was such that the reaction mixture stayed hot throughout the addition and did not require external heating.

After complete addition of the Grignard solution the reaction mixture was heated by an oil bath at a bath temperature of 80°–100° C. for 18 hr after which time the mixture had become pure white.

Pure trimethylgallium (boiling point 56° C.) was obtained by distillation through a 30 cm×1.5 cm column packed with glass beads or Fenske helices. The bath temperature during distillation was higher than 180° C. (~200° C.). Only one fraction was collected.

The yield of $(CH_3)_3Ga$ was 11.0 g (67.5% based on the amount of gallium trichloride used).

The product structure was checked by mass spectrometry using a VG Micromass 13 mass spectrometer using the batch inlet, and the results are given in Table 1 as follows.

TABLE 1

MASS SPECTRAL DATA FOR THE PRODUCT OF EXAMPLE 2 mass: charge ratio (assignment): 69/71 $[Ga]^+$
84/86 $[Me\ Ga]^+$   99/101 $[ME_2\ Ga]^+$
114/116 $[Me_3\ Ga]^+$
[Source temperature = 120° C., Ionisation energy = 30 eV]

The data in Table 1 confirms that the product was trimethyl gallium.

Trimethyl gallium may be prepared by a method analogous to the above example but using anisole (preferably at a reaction temperature of about 90°–100° C.) or alternatively diphenyl ether (preferably at a reaction temperature of about 80°–90° C.) as solvent in the Grignard reagent/gallium trichloride reaction. In these alternatives distillation of trimethyl gallium from the intermediate adducts is carried out using oil bath temperatures of about 150° C. (for the anisole adduct) and 140° C. (for the diphenyl ether adduct) respectively.

Trimethyl gallium samples produced by the method of the above example have proved suitable for use in growing high quality epitaxial layers of GaAs (from the reaction of $Ga(CH_3)_3$ and $AsH_3$) with carrier concentrations of from 3 to $4.5 \times 10^{15}\ cm^{-3}$ at 298K which are better quality layers than those produced from commercially available trimethyl gallium.

We claim:

1. A method of providing a trialkyl gallium compound having the formula $(R_A)_3Ga$ wherein said formula $R_A$ is independently selected from methyl and ethyl, said method comprising the steps of:
   (a) forming an ether adduct of said trialkyl gallium compound, said ether adduct having the formula $(R_A)_3Ga.R_1R_2O$ by reacting, in a mixture, a gallium trihalide with a Grignard reagent in the presence of an ether, said Grignard reagent having the formula $R_aMgQ$ wherein Q is a halogen and each $R_A$ is independently selected from methyl and ethyl, said ether having a boiling point at least 50° C. above said trialkyl gallium compound, said ether having the formula $R_1R_2O$ wherein $R_1$ and $R_2$ are independently selected from alkyl and phenyl radicals such that when $R_1$ and $R_2$ are both alkyl at least one of $R_1$ and $R_2$ has at least five carbon atoms; and
   (b) heating said ether adduct to provide dissociation thereof thereby releasing said trialkyl gallium compound of the formula $(R_A)_3Ga$ into the vapor phase.

2. The method according to claim 1 wherein $R_1$ and $R_2$ together have from 7 to 12 carbon atoms.

3. The method according to claim 1, wherein said ether has boiling point more than 100° C. greater than that of said trialkyl gallium compound.

4. The method according to claim 1, wherein said ether is selected from the group consisting of diisopentyl ether, diphenyl ether and anisole.

5. The method according to claim 4, wherein said ether is diisopentyl ether.

6. The method according to claim 1, wherein said Q is iodine.

7. The method according to claim 1, wherein said gallium trihalide is gallium trichloride.

8. The method according to claim 1, wherein the compound $(R_A)_3Ga$ is subsequently separated from the vapor phase product of step (b) by fractional distillation.

9. The method according to claim 8, wherein prior to step (b) the volatile impurities are removed from the mixture by evacuation at a temperature below the dissociation temperature of the ether adduct.

10. The method according to claim 1, wherein step (a) is carried out at a temperature in the range of 70° C. to 110° C. and said trialkyl gallium is trimethyl gallium.

* * * * *